United States Patent [19]
Cowsar et al.

[11] Patent Number: 5,085,866
[45] Date of Patent: Feb. 4, 1992

[54] METHOD OF PRODUCING ZERO-ORDER CONTROLLED-RELEASED DEVICES

[75] Inventors: Donald R. Cowsar, Birmingham, Ala.; Richard L. Dunn, Fort Collins, Colo.; Thomas J. Laughlin, Germantown, Tenn.

[73] Assignee: Southern Research Institute, Birmingham, Ala.

[21] Appl. No.: 279,216

[22] Filed: Dec. 2, 1988

[51] Int. Cl.$^5$ .............................................. A61K 9/14
[52] U.S. Cl. ................................... 424/481; 424/482; 424/480; 424/475; 427/3
[58] Field of Search ............... 424/475, 480, 481, 482; 427/3

[56] References Cited

U.S. PATENT DOCUMENTS 4,572,833 2/1986 Pedersen et al. ................... 427/3
4,713,243 12/1987 Schiraldi et al. ................... 424/449

Primary Examiner—Thurman Page
Assistant Examiner—Louis A. Piccone
Attorney, Agent, or Firm—Needle & Rosenberg

[57] ABSTRACT

An improved method of producing a reservoir device having a rate-controlling membrane and zero-order (constant) release of an agent is provided. A core is sprayed with a solution having a polymer and a solvent, the solvent having a first component which is a rapidly evaporating, low-boiling-point first solvent and a slowly evaporating, high-boiling-point second solvent.

17 Claims, 4 Drawing Sheets

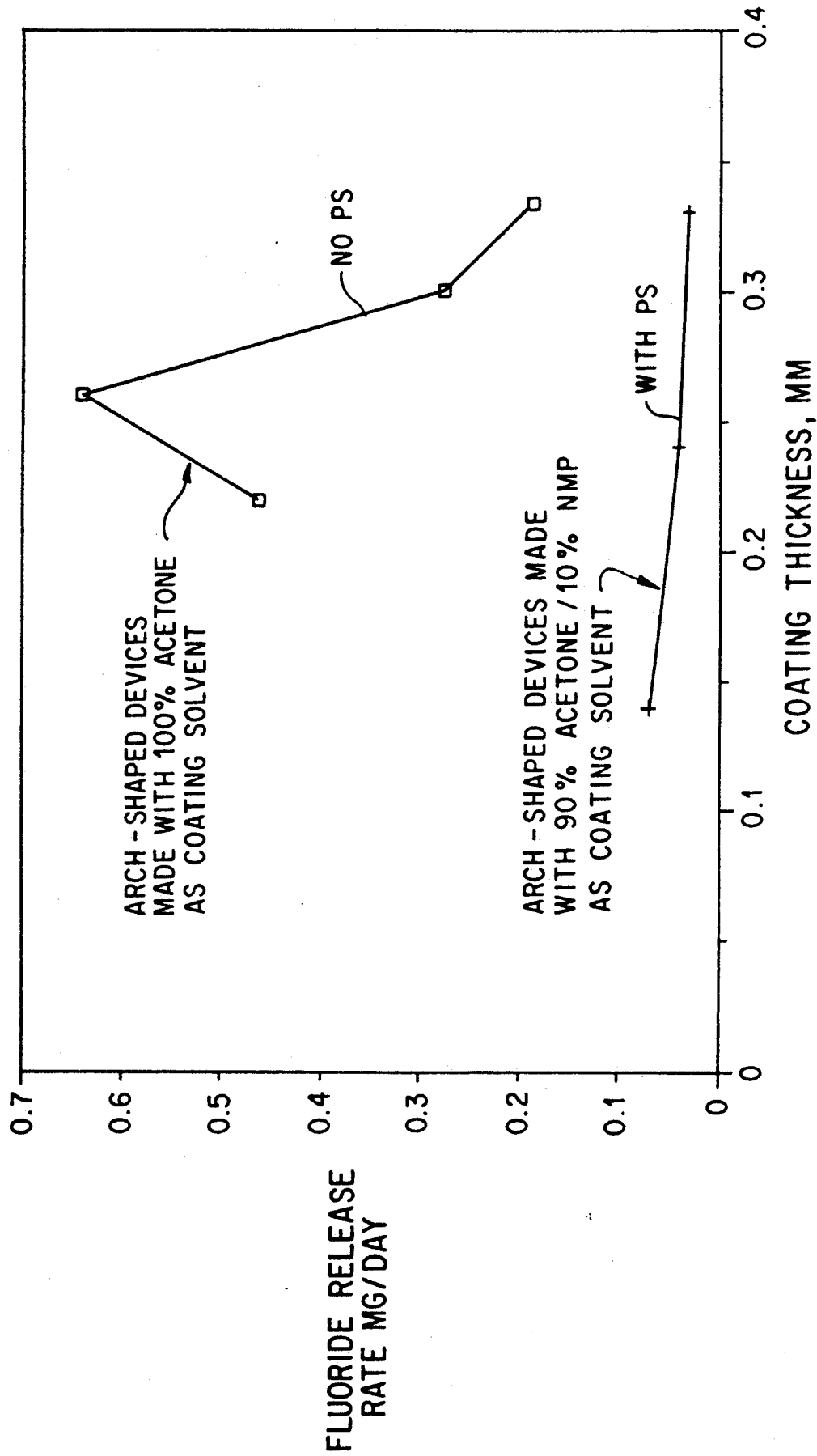

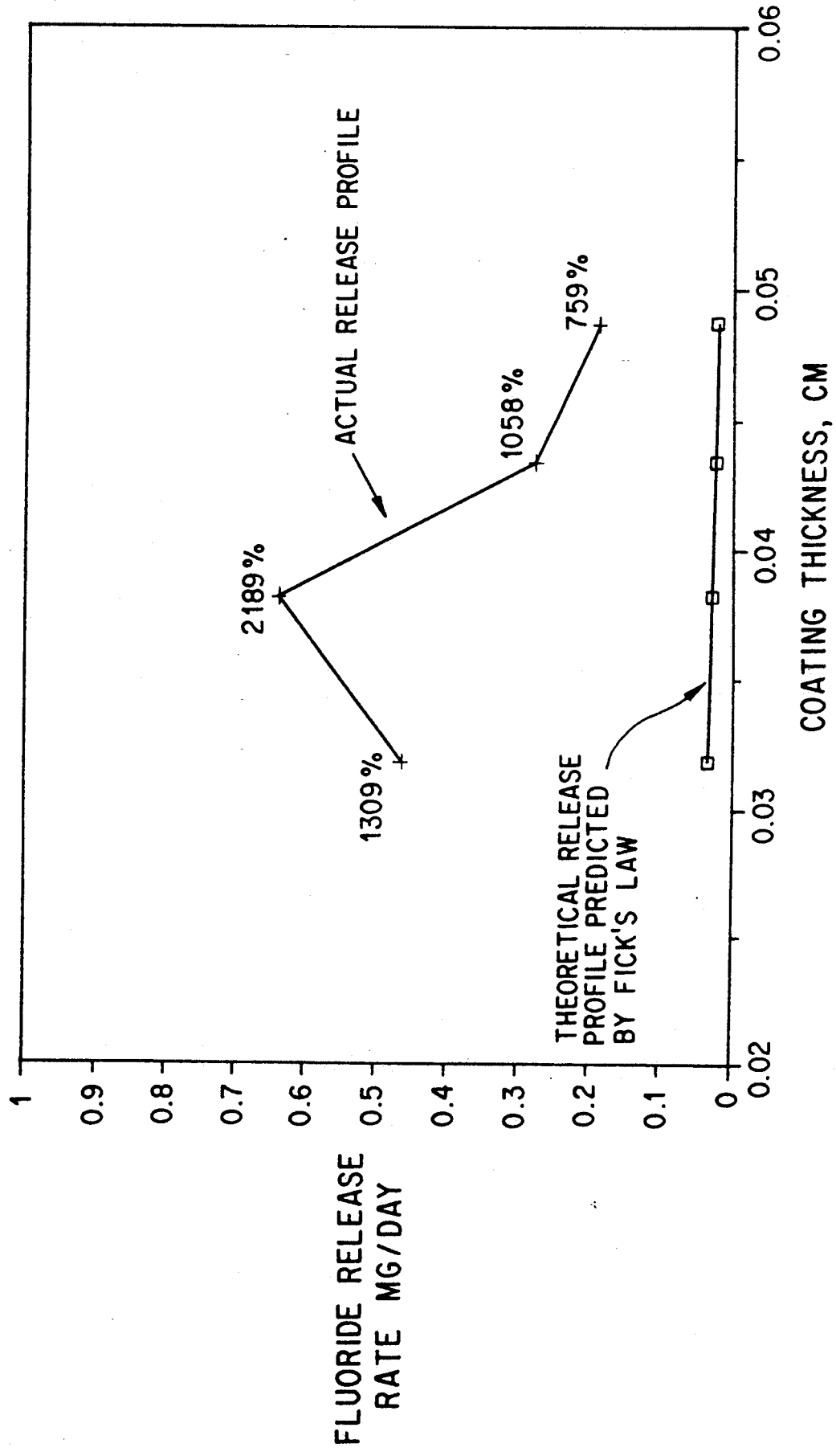

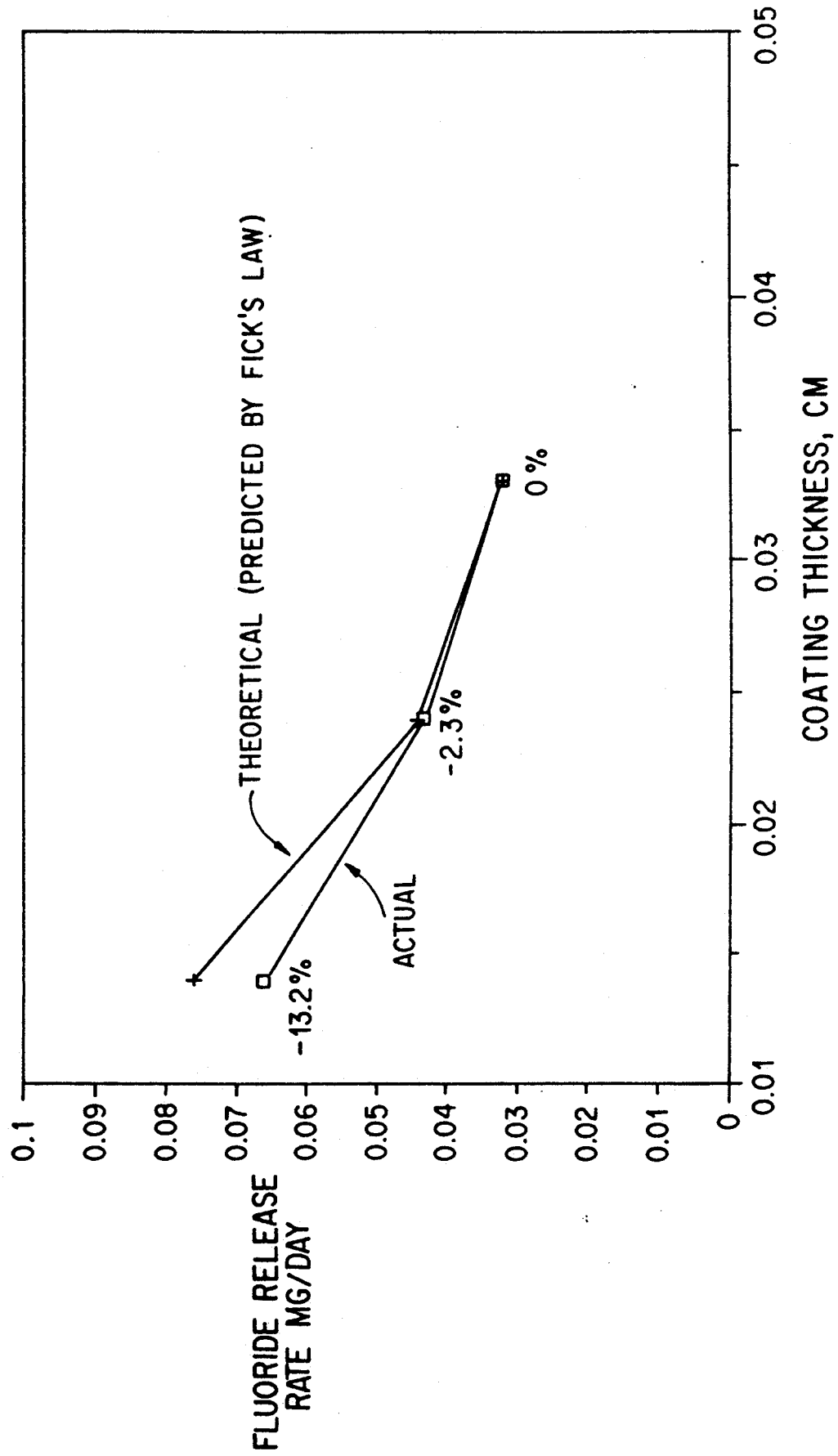

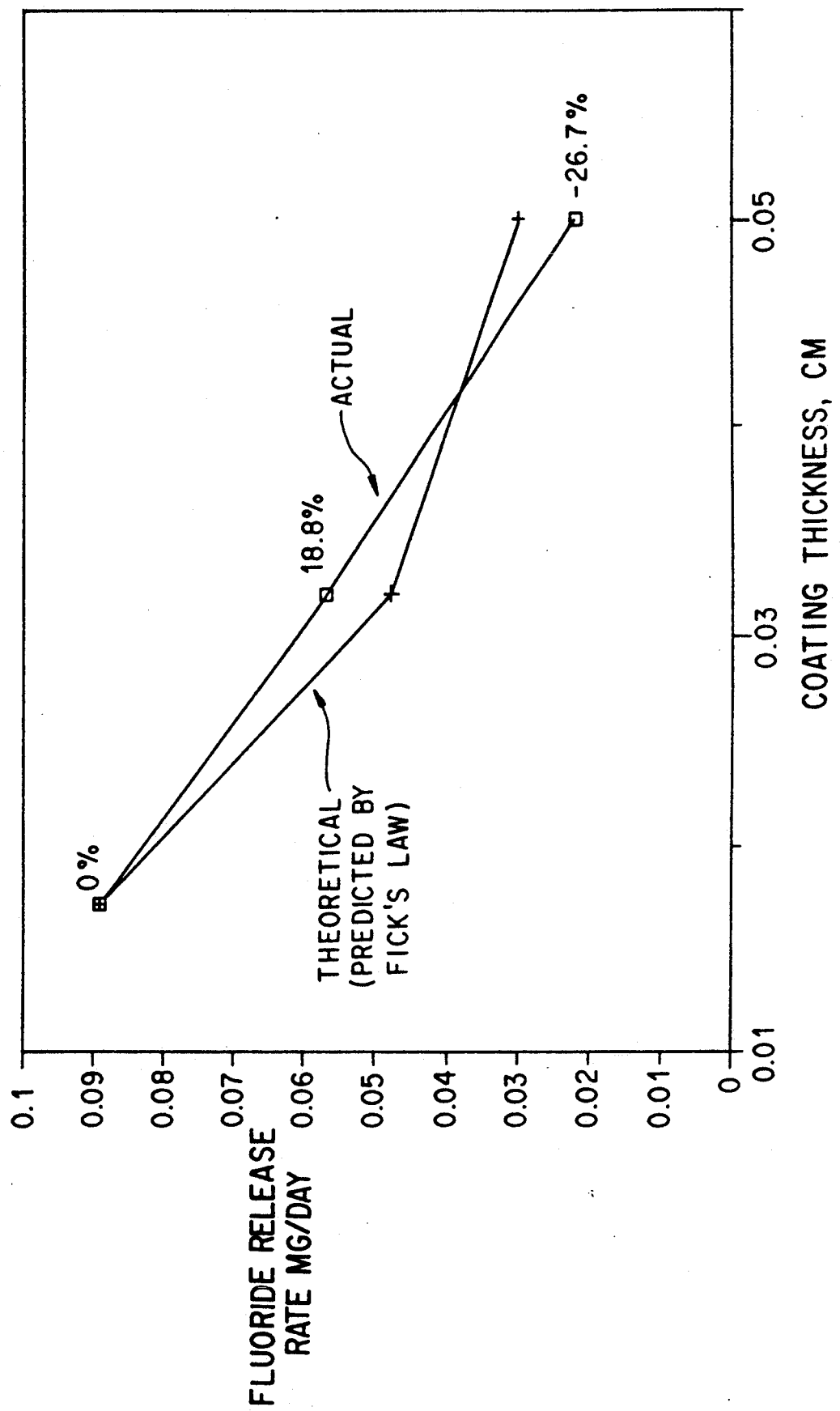

METHOD OF PRODUCING ZERO-ORDER CONTROLLED-RELEASED DEVICES

BACKGROUND OF THE INVENTION

The present invention relates to an improved method of producing zero-order controlled-release devices.

Zero-order controlled-release devices are well known and have many uses. For example, Cowsar et al. (D. R. Cowsar, O. R. Tarwater, and A. C. Tanquary,) in their article "Controlled Release of Fluoride from Hydrogels for Dental Applications", in ACS Symposium Series, No. 31, *Hydrogels for Medical and Related Applications*, Joseph D. Andrade, Ed., American Chemical Society, Washington, D.C., p. 180, (1976) describes an intraoral fluoride-releasing device suitable for delivering sodium fluoride in the mouth continuously for six months. The device comprised a core of sodium fluoride entrapped in a 50:50 hydroxyethyl methacrylate (HEMA):methyl methacrylate (MMA) copolymer and a Fick's Law membrane coating of 30:70 HEMA:MMA. Devices were prepared singularly in two steps by (1) adding 60:40 acetone: p-dioxane to a mixture of 60 to 80 wt% sodium fluoride and 40 to 20% 50:50 HEMA:MMA to make a thick paste which was cast in precision cavity molds and dried, and (2) dipping the fluoride-containing cores repeatedly into a 12 wt% solution of 30:70 HEMA:MMA in 60:40 acetone:p-dioxane and allowing the solvent to evaporate between each dipping to form a Fick's Law membrane encasing the cores.

Moreover, Cowsar et al. have shown that these devices are extremely promising in preventing dental caries in man (D. R. Cowsar, T. R. Tice, and D. B. Mirth, "An Intraoral Fluoride-Releasing Device for Prevention of Dental Caries", in Proceedings of the 12th International Symposium on Controlled Release of Bioactive Materials, N. A. Peppas and R. J. Haluska, Eds, Geneva, Switzerland, p. 310, 1985).

The intraoral fluoride-releasing devices described above are just one classic reservoir-type devices having zero-order (constant) release kinetics. Such devices obey Fick's Law of Diffusion because the rate of release of agent, such as fluoride, from the device varies directly with the surface area of the device and inversely with the thickness of the rate-controlling membrane. Because these devices typically deliver drugs, both the rate and the duration of release must be controlled precisely for maximum therapeutic effect with a minimum of toxicity.

Unfortunately, the full potential for this technology has not been met. The laboratory manufacturing process used to produce these devices is laborious and time consuming. For example, for each device produced by the above-described process, approximately 20 minutes was required between each dipping and approximately 14 dippings were required to produce a rate-controlling membrane of about 0.01 cm in thickness. Although that laboratory dipping process could be "scaled-up" to produce numerous devices simultaneously, the manufacturing in commercial quantities requires producing 10,000 or more devices in one batch operation. Also, the current method results in a large amount of residual p-dioxane.

Furthermore, the current method of applying the core around the agent is also problematic. According to the traditional method of coating in a fluidized-bed process, the cores are suspended in an upward-flowing column of hot air, and a solution of the coating polymer is sprayed continuously onto the fluidized bed of tumbling cores. As solvent/polymer microdroplets strike the surface of the cores, the droplets spread on the surface until the solvent evaporates, thereby leaving a "piece" of polymer coating deposited on the core. The process is continued until the cores become fully coated, and then it is continued further until the coating thickness builds to the desired level.

Because the coating has to function as a rate-controlling membrane that obeys Fick's Law of Diffusion, it requires homogeneous, continuous coatings without either gross or micro defects. However, the currently used single solvent process does not provide Fickian membranes. In the current fluidized-bed processes, the solvent for the coating polymer must evaporate fast enough so that the surfaces of the cores never become sticky. If they become sticky, twinning (two fused cores) or gross agglomeration occurs. On the other hand, if the solvent evaporates too quickly, the polymer coating is deposited as discrete heterogeneous particles or flakes. Heterogeneous coatings do not obey Fick's Law of diffusion because the drug is released at a fast rate through discontinuities in the coating.

Therefore, there exists a need for an improved method of producing zero-order, controlled-released devices.

There also exists a need for a cost efficient method of producing such devices on a large-scale basis.

There exists a further need for an improved method of producing a device which releases fluoride at a zero-order controlled rate over a long period of time.

SUMMARY OF THE INVENTION

The present invention relates to an improved method of producing a reservoir device having a zero-order rate-controlling membrane. A core containing agent is coated in a fluidized bed coating apparatus with a coating solution comprised of a polymer dissolved in a mixed solvent system. The solvent is comprised of a low-boiling, rapidly evaporating solvent and a high-boiling, slowly evaporating plasticizing solvent.

During coating, the cores are suspended in an upward-flowing column of hot air, and a solution of the coating is sprayed continuously onto the fluidized bed of tumbling cores. The temperature in the apparatus is maintained as close as possible to the boiling point of the plasticizing solvent without exceeding it. The plasticizing solvent, therefore, remains in the deposited microdroplet so that when additional microdroplets are deposited, the microdroplets fuse to form a continuous homogeneous membrane. The resulting coating is free from gross and micro defects and exhibits zero-order controlled release of agent.

The core agent may also be mixed with a polymer before coating to insure first-order release in the event of a failure of the outer coating. To maintain zero-order release through the device, the polymer inside the core must be more permeable to the agent than the coating polymer.

The present invention has been found to be particularly useful in producing intraoral devices which continuously release fluoride at a controlled rate to the oval cavity for periods of up to six months or more. A preferred composition of the device of the present invention comprises a core of sodium fluoride entrapped in a 50:50 (mole ratio) hydroxyethyl methacrylate (HEMA): methyl methacrylate (MMA) copolymer and a Fick's Law outer coating of 20:80 (mole ratio) HEMA:MMA. The devices were prepared using a solvent solution comprising 90 wt% acetone and 10 wt% N-methylpyrrolidone (NMP).

It is, therefore, an object of the present invention to provide an improved method of producing zero-order, controlled-release devices.

It is another object of the present invention to provide such a method which is cost efficient and can be performed on a large-scale basis.

It is still another object of the present invention to provide an improved method of producing a device which releases fluoride at a zero-order release rate over a long period of time.

These and other objects and advantages of the present invention are set forth in the following detailed description of the present invention.

BRIEF DESCRIPTION OF THE FIGURES

FIGS. 1 and 2 compare the release rates of devices made with and without a plasticizing solvent in the coating solution; and FIG. 3 illustrates that devices produced with 90:10 wt% acetone:NMP obey Fick's Law very closely.

FIG. 4 illustrates that compositions made according to the invention obey Fick's Law very closely.

DETAILED DESCRIPTION OF THE INVENTION

The present invention relates to an improved method for producing zero-order, controlled-release devices utilizing a fluidized-bed coating apparatus. The resulting device has a homogeneous, continuous Fickian membrane which is free from gross or micro defects.

The method according to this invention comprises the steps of first forming a core containing an agent, then spraying a solution having a polymer dissolved in a solvent onto the core to form a diffusion-rate-controlling membrane coating. The solvent is comprised of a first component which is a rapidly evaporating chemical and a second component which is a slowly evaporating, plasticizing chemical having a boiling point greater than that of the first component. After the coating is complete, the first component is allowed to evaporate and the second, plasticizing component is removed. The resulting structure is a device having a homogeneous, continuous coating free from either gross or micro defects and which obeys Fick's Law of Diffusion. The rate of release of agent is independent of the concentration of agent in the core.

The core which may be coated in accordance with the process of this invention includes medicaments, nutrients, and any other agent capable of diffusing through the polymer coating. Typically, agents having molecular weights of approximately 1000 or less will diffuse through the coating. Examples of potential agents include, among others, sodium fluoride, sodium monofluorophosphate, xylocaine, tetracycline, lidocaine, steroids, pilocarpine, nitroglycerine, antibiotics, peptides, phenobarbital, analgesics and narcotic antagonists.

The cores may be of any suitable size and shape as dictated by the eventual purpose of the device. One important consideration is that the core must be hard enough to withstand the tumbling associated with coating in a fluidized-bed apparatus. A hardness of 3.5 Kg and above (as measured by a Pfizer Hardness Tester, available from Testing Machines, Amityville, N.Y.) has been found to be sufficient. It has been found that cores made at higher compression pressures and with large fluoride particles stand to have the highest hardness values. While the core may be formed by any method providing these desired characteristics, it has been found that grinding the agent to a powder and then tableting the agent in a tableting press, such as a Stokes Model 511-6 single-position laboratory press available from Pennwalt Corp., Philadelphia, Pa., or an equivalent multicavity, high-speed, high-volume machine is preferred.

Once the cores are prepared, they are placed within a fluidized-bed coating apparatus for application of the zero-order, controlled-release membrane. A solution comprising effective amounts of a polymer dissolved in a solvent is sprayed onto the core to form a homogeneous membrane.

A mixed solvent system has been found to provide the defect-free, continuous Fickian membrane essential for zero-order release. The solvent system has a low-boiling, fast-evaporating solvent as a major component and a high-boiling, slow-evaporating, plasticizing solvent as a minor component. The solvent mixture should contain between approximately 5 to 50 wt% plasticizing solvent and 95 to 50 wt% fast-evaporating solvent.

During coating, the plasticizing solvent remains in the deposited microdroplet while the fast-evaporating solvent evaporates, and the microdroplets fuse to form a continuous homogeneous membrane. For this reason, the temperature within the fluidized-bed apparatus should be as close as possible to, but not meeting or exceeding, the boiling point of the plasticizing solvent. The difference between the boiling points of the two solvents should also be as great as possible. Also, the temperature of the coating process should take into account the decomposition limits of the drug and polymer.

Examples of plasticizing solvents include, among others, N-methylpyrrolidone (NMP), dioxane, dimethyl sulfoxide, hexamethyl phosphoramide, phthalatec esters, salicylate esters, glycerine, ethylene glycol, propylene glycol, ethylene glycol monomethyl ether, xylene, t-butanol water and N,N-dimethylacetamide. Examples of fast-evaporating solvents include, among others, acetone, methylethylketone, ethyl acetate, methyl acetate, dichloromethane, chloroform, hexane, heptane, cyclohexane, freons, benzene, toluene, petroleum ether, mineral spirits, ethanol, methanol and propanol.

Any thermoplastic polymer or copolymer may be utilized in the present invention so long as it can be dissolved in the solvent and deposited onto the core. However, amorphous polymers are preferred over crystalline polymers. Examples of such polymers and copolymers include, among others, polymethyl methacrylate, polyhydroxyethyl methacrylate, poly (ethyl acrylate), cellulose acetate, ethyl cellulose, methyl cellulose, cellulose acetate-butyrate, hydroxypropyl cellulose, polyethylene, poly (ethylene-vinyl acetate), poly-(ethylene-acrylic acid), polystyrene, polycarbonate, polyamides, poly(ethylene terephthalate), polyether-polyurethane and polyester-polyurethane block copolymers, and polyacetals. In some instances, the nature of the agent must be considered in choosing the polymer. For instance, a HEMA/MMA copolymer may be most useful with a water soluble or hydrophilic agent, while an ethylene/vinylacetate copolymer may be used with the lipophilic steroids and most other drugs. The primary consideration is that the agent must be diffusible through the polymeric coating.

A second polymer may be placed in the core to entrap the agent and to insure first-order release of agent if the outer membrane is damaged. Although any biocompatible polymer may be used, it is necessary that the core polymer be more permeable to the agent than the coating polymer. The diffusion of agent will, therefore, depend solely on the outer, Fickian membrane.

Once the coating has been applied, it may be necessary to remove any residual plasticizing solvent. Otherwise, the residual solvent could affect both the permeability of the coating membrane and the potential toxicity of the device. This may be accomplished by extracting the device with water, an alcohol such as ethanol or isopropanol, or a combination of water and alcohol. Another option is placing the device in an organic solvent for the plasticizing agent but not for the polymers. The rate of extraction may be increased by heating the extracting solution.

EXAMPLE

The following example sets forth one, specific embodiment of the invention relating to the production of a high quality intraoral fluoride releasing devices for providing a continued topical release of fluoride into the oral cavity of a subject for the prevention of dental cavities over an approximate six-month period. Depending on the membrane coating thickness, the devices release in the range from 0.04 to 0.20 mg of fluoride per day. It should be recognized, however, that the present invention may be utilized whenever homogeneous continuous coatings are desired to provide a zero-order, controlled-release device having minimal gross or micro defects.

A core comprising a mixture of granulated 80 wt% sodium fluoride and 20 wt% 50:50 (mole ratio) hydroxyethyl methacrylate/methylmethacrylate (HEMA/MMA) copolymer is produced. The core is made by tableting the mixture into individual tablets weighing from between 35 to 65 mg and having a hardness over 3.5 Kg. The tablets are arched shaped to fit the curved surface of a tooth.

The tableted cores are then placed in a Wurster-type, industrial fluidized-bed coating apparatus and coated with a solution of 1 wt% 20:80 (mole ratio) HEMA/MMA dissolved in 10 wt% N-methyl-2-pyrrolidone/90 wt% acetone. The N-methyl-2-pyrrolidone has a boiling point of about 202° C. and is an exceptionally good plasticizing solvent for applying the HEMA/MMA copolymer membranes to the core. The acetone has a boiling point of about 57° C. and is used as the fast-evaporating solvent. The temperature inside the apparatus is set at approximately 175° C., and the cores are coated continuously until the coating comprises about 10 to 35% of the total weight of the device. The solution is preferably delivered to the apparatus at a rate of about 1.5 mL/hr/gram of cores. To prevent cracking of the coating, the column containing the coated cores should be cooled slowly, i.e., at a rate of approximately 10 per minute.

Once properly coated, the devices may contain up to 2.5% by weight residual NMP. It has been found that this can be reduced by more than a factor of 10 (to <0.2%) by placing the devices in water at room temperature for approximately 48 hours. Alternatively, since the extraction rates approximately double for every 10° C. rise in temperature, the device may be extracted in 100° C. water for about 20 minutes. The presence of either sodium fluoride or sodium chloride in the extracting bath will reduce the likelihood that sodium fluoride will be extracted prematurely from the devices. Alternatively, the device may be extracted in a solvent for NMP that is not a solvent for the HEMA/MMA. Examples of such solvents include hexane, heptane, a fluorinated hydrocarbon such a freon, or an edible oil such as corn oil or mineral oil. It has been found that the amount of residual solvent in each device is less than 1 wt% of total device weight after extraction.

For the fluoride-releasing devices, the water extraction process also causes the coating to hydrate, thereby saturating the rate-controlling membrane with sodium fluoride and enabling the device to immediately diffuse the agent upon implantation in a subject.

The resulting intraoral devices were found to exhibit exceptionally accurate zero-order controlled-release of fluoride. FIG. 1, entitled "EFFECT OF PLASTICIZING SOLVENTS", summarizes an analysis of identical arch-shaped devices made according to the above example with and without the plasticizing solvent (NMP) in the coating solution. The devices made without the NMP (i.e., with acetone alone) released fluoride at a much higher rate than is predicted by Fick's Law, as shown in FIG. 2, entitled "WITHOUT PLASTICIZING SOLVENT". Moreover, FIG. 3, entitled "ACTUAL VS. THEORETICAL RELEASE", illustrates that devices made with 90:10 wt% acetone:NMP very closely obey Fick's Law. The theoretical curves were calculated using the measured diffusion coefficient ($D = 8.0 \times 10^{-8} cm^2 sec^{-1}$) and saturation solubility ($Cs = 2.5 \times 10^{-4} gF/cm^3$). An additional benefit of this device is that dioxane has been eliminated from the manufacturing process.

What it is claimed is:

1. An improved method of producing a reservoir device having a zero-order rate controlling membrane, comprising the steps of:
   (a) spraying a solution onto a core comprised of an agent to form a rate controlling membrane coating thereon, said solution comprising effective amounts of a first polymer and a solvent having a first component which is a rapidly evaporating solvent having a first boiling point and a second component which is a slowly evaporating plasticizing solvent having a second boiling point higher than said first boiling point;
   (b) allowing said first component to evaporate from said coating; and
   (c) removing said plasticizing solvent from said coating.

2. The method of claim 1, wherein said solvent comprises 5 to 50 wt% NMP and 95 to 50 wt% acetone.

3. The method of claim 1, wherein said solvent comprises approximately 10 wt% NMP and approximately 90 wt% acetone.

4. The method of claim 1, wherein said first polymer is a copolymer of HEMA and NMA and wherein said copolymer is present in a concentration of approximately 1.0 to 1.75 wt% of said solution.

5. The method of claim 1 wherein said first polymer is a copolymer comprising between approximately 10 to 30 wt% HEMA and 90 to 70 wt% MMA.

6. The method of claim 1 wherein said first polymer is a copolymer comprising approximately 20 wt% HEMA and 80 wt% MMA.

7. The method of claim 1, wherein the temperature during said spraying step is above the boiling point of said first component and below the boiling point of said second component.

8. The method of claim 1, and further comprising the step of forming said core prior to said spraying step, wherein said core forming step comprises the step of mixing a second polymer with said agent to produce said core, said second polymer being more permeable to said agent than said first polymer.

9. The method of claim 8, wherein said first polymer is a copolymer comprising between approximately 10 to 30 wt% HEMA and 90 to 70 wt% MMA, and said second polymer is a copolymer comprising approximately a 50:50 (mole ratio) HEMA/MMA.

10. The method of claim 1, wherein said solution is prepared by dissolving approximately 1 to 15 wt% of 20:80 (mole ratio) HEMA/MMA in a solvent mixture comprising 90 wt% acetone and 10 wt% NMP.

11. The method of claim 1, wherein said removing step comprises extracting said device with water.

12. The method of claim 11, wherein said agent is sodium fluoride and said water contains an effective amount of a sodium salt.

13. The method of claim 11, wherein said water contains an effective amount of an alcohol.

14. The method of claim 1, wherein said removing step comprises extracting said device with alcohol.

15. The method of claim 1, wherein said removing step comprises extracting said device with an organic solvent for said plasticizing solvent that is not a solvent for said polymer.

16. The method of claim 15, wherein said organic solvent is selected from the group consisting essentially of hexane, heptane, a fluorinated hydrocarbon or an edible oil.

17. The method of claim 15, wherein said first polymer is a HEMA/MMA copolymer, said plasticizing solvent is NMP, and said organic solvent is selected from the group consisting essentially of hexane, heptane, a fluorinated hydrocarbon, or an edible oil.

* * * * *